United States Patent
Finger

(10) Patent No.: US 11,998,384 B2
(45) Date of Patent: Jun. 4, 2024

(54) APPARATUSES, SYSTEMS, AND METHODS FOR CONVEYING IMPLEMENTS THROUGH A NARROW PASSAGE IN A BODY

(71) Applicant: Gyrus ACMI Inc., Southborough, MA (US)

(72) Inventor: Clinton L. Finger, Seattle, WA (US)

(73) Assignee: Gyrus ACMI, Inc., Westborough, MA (US)

(*) Notice: Subject to any disclaimer, the term of this patent is extended or adjusted under 35 U.S.C. 154(b) by 233 days.

(21) Appl. No.: 17/029,102

(22) Filed: Sep. 23, 2020

(65) Prior Publication Data
US 2021/0093290 A1 Apr. 1, 2021

Related U.S. Application Data

(60) Provisional application No. 62/906,601, filed on Sep. 26, 2019.

(51) Int. Cl.
*A61B 8/08* (2006.01)
*A61B 8/12* (2006.01)
(Continued)

(52) U.S. Cl.
CPC .............. *A61B 8/0841* (2013.01); *A61B 8/12* (2013.01); *A61B 10/0283* (2013.01);
(Continued)

(58) Field of Classification Search
CPC ..... A61B 8/0841; A61B 8/12; A61B 10/0283; A61B 17/3423; A61B 18/1482;
(Continued)

(56) References Cited

U.S. PATENT DOCUMENTS

2004/0254572 A1* 12/2004 McIntyre ........... A61B 18/1477
606/41
2005/0148953 A1* 7/2005 Fulton, II ....... A61B 17/320758
604/266
(Continued)

FOREIGN PATENT DOCUMENTS

CN 112545635 A 3/2021
EP 2982330 2/2016
(Continued)

OTHER PUBLICATIONS

Jan. 19, 2022, French Patent Office issued an office action with cited references for French Application No. FR2009740.
(Continued)

*Primary Examiner* — Ashley K Buran
*Assistant Examiner* — Kaitlyn E Sebastian
(74) *Attorney, Agent, or Firm* — Schwegman Lundberg & Woessner, P.A.

(57) ABSTRACT

Disclosed embodiments include apparatuses, systems, and methods for conveying implements through a narrow passage in a body. In an illustrative embodiment, an insertion tube defines therein lumens and is configured to slide through an orifice and into a passageway to a target tissue. A first probe is connectable to a power source, is slidably receivable through one of the lumens, and has a distal end insertable into the target tissue. An imaging probe is connectable to an imaging device configured to collect imaging data at a distal end, is slidable through one of the lumens not receiving the first probe, and is positionable to collect imaging data at a distal end of the insertion tube. A second probe is connectable to the power source, is slidably receivable through one of the lumens not receiving the first probe, and has a distal end insertable into the target tissue.

13 Claims, 10 Drawing Sheets

(51) Int. Cl.
| | |
|---|---|
| *A61B 10/02* | (2006.01) |
| *A61B 17/34* | (2006.01) |
| *A61B 18/14* | (2006.01) |
| *A61B 1/018* | (2006.01) |
| *A61B 1/267* | (2006.01) |
| *A61B 17/00* | (2006.01) |
| *A61B 18/00* | (2006.01) |
| *A61B 18/12* | (2006.01) |

(52) U.S. Cl.
CPC ...... *A61B 17/3423* (2013.01); *A61B 18/1482* (2013.01); *A61B 1/018* (2013.01); *A61B 1/2676* (2013.01); *A61B 2017/00867* (2013.01); *A61B 2017/00973* (2013.01); *A61B 2017/3413* (2013.01); *A61B 2017/3425* (2013.01); *A61B 2017/3445* (2013.01); *A61B 2018/00077* (2013.01); *A61B 2018/00541* (2013.01); *A61B 2018/00577* (2013.01); *A61B 2018/00589* (2013.01); *A61B 2018/00601* (2013.01); *A61B 2018/1253* (2013.01); *A61B 2018/126* (2013.01)

(58) Field of Classification Search
CPC ................. A61B 1/018; A61B 1/2676; A61B 2017/00867; A61B 2017/00973; A61B 2017/3413; A61B 2017/3425; A61B 2017/3445; A61B 2018/00077; A61B 2018/00541; A61B 2018/00577; A61B 2018/00589; A61B 2018/00601; A61B 2018/1253; A61B 2018/126; A61B 8/085; A61B 8/445; A61B 18/1492; A61B 90/37; A61B 2017/345; A61B 2018/00166; A61B 2018/00273; A61B 2018/00279; A61B 2018/00982; A61B 2018/1435; A61B 18/12; A61B 18/1477; A61B 1/01; A61B 17/3421; A61B 18/14; A61B 2017/3447; A61B 2018/1412; A61M 25/01

See application file for complete search history.

(56) References Cited

U.S. PATENT DOCUMENTS

| | | | |
|---|---|---|---|
| 2006/0085054 A1* | 4/2006 | Zikorus | A61B 18/08 607/113 |
| 2006/0178665 A1* | 8/2006 | Sloan | A61B 18/1477 606/41 |
| 2008/0009747 A1 | 1/2008 | Saadat et al. | |
| 2009/0093726 A1* | 4/2009 | Takayama | A61B 8/4488 600/466 |
| 2010/0057078 A1* | 3/2010 | Arts | A61B 17/0469 606/1 |
| 2014/0163327 A1 | 6/2014 | Swanstrom | |
| 2014/0180250 A1* | 6/2014 | Belson | A61M 25/0097 604/510 |
| 2015/0305801 A1 | 10/2015 | Trieu | |
| 2016/0022353 A1* | 1/2016 | Forsyth | A61B 34/10 606/34 |
| 2016/0263401 A1* | 9/2016 | Lu | A61B 5/0066 |
| 2019/0231466 A1 | 8/2019 | Weitzner et al. | |
| 2019/0254649 A1* | 8/2019 | Walters | A61B 1/07 |

FOREIGN PATENT DOCUMENTS

| | | | | |
|---|---|---|---|---|
| EP | 3263061 | | 1/2018 | |
| FR | 3101531 | A1 | 4/2021 | |
| GB | 2590139 | | 6/2021 | |
| JP | 2021053390 | A | 4/2021 | |
| WO | 2008101086 | A2 | 8/2008 | |
| WO | WO-2008101086 | A2 * | 8/2008 | ............ A61B 1/018 |
| WO | 2010080974 | A1 | 7/2010 | |
| WO | 2015153931 | A1 | 10/2015 | |
| WO | WO-2015153931 | A1 * | 10/2015 | ............ A61B 1/012 |
| WO | 2019172318 | | 9/2019 | |

OTHER PUBLICATIONS

"United Kingdom Application Serial No. 2015167.6, Search Report under Section 17(5) dated Mar. 4, 2021", 6 pgs.

"French Application Serial No. 2009740, Office Action dated Mar. 3, 2021", w/o English Translation, 2 pgs.

"United Kingdom Application Serial No. 2015167.6, First Examination Report Under Section 18(3) dated Mar. 2, 2023", 3 pgs.

* cited by examiner

APPARATUSES, SYSTEMS, AND METHODS FOR CONVEYING IMPLEMENTS THROUGH A NARROW PASSAGE IN A BODY

PRIORITY CLAIM

The present application claims the priority and benefit of U.S. Provisional Patent Application Ser. No. 62/906,601 filed Sep. 26, 2019 and entitled "APPARATUSES, SYSTEMS, AND METHODS FOR CONVEYING IMPLEMENTS THROUGH A NARROW PASSAGE IN A BODY."

FIELD

The present disclosure relates to conveying implements through a narrow passage in a body.

BACKGROUND

The statements in this section merely provide background information related to the present disclosure and may not constitute prior art.

Inserting and manipulating thin elements within living bodies or other objects allows for ever-improving types of analysis, diagnosis, and treatment of those bodies or objects with minimally invasive techniques. By way of two examples, endoscopic imaging and catherization treatments have enabled evaluation and treatment of numerous internal lesions without invasive surgery.

Electrosurgical techniques also provide for minimally invasive therapies by selectively applying electrical current to selected tissues. Electrosurgical techniques involve inserting one or more electrodes through an orifice or a small incision and then extending the one or more electrodes to a desired location within a body of a patient. A radio frequency ("RF") electric current is then applied to the electrodes to coagulate, ablate, or otherwise treat tissue at that location. Monopolar electrosurgical instruments involve the insertion of one electrode that electrically interacts with a second electrode that is electrically connected to the body of the patient. A bipolar electrosurgical instrument involves the deploying of two electrodes at the location within the body of the patient where treatment is to be administered.

Positioning one or two electrodes at the desired location in a patient's body is an important part of electrosurgical treatments. Electrosurgical devices, such as endoscopic or bronchoscopic devices may be useful in conveying electrodes to target regions in a body. Some bodily passageways, however, may be too narrow to permit the insertion of some electrosurgical devices.

SUMMARY

Disclosed embodiments include apparatuses, systems, and methods for conveying implements through a narrow passage within a body.

In an illustrative embodiment, an apparatus includes an insertion tube defining therein lumens, the insertion tube being configured to slide through a bodily orifice and into a bodily passageway to a target tissue. A first electrically-conductive elongated probe is electrically connectable to a first pole of an electrical power source. The first probe is slidably receivable through one of the plurality of lumens and has a distal end insertable into the target tissue. An elongated imaging probe is electrically connectable to an imaging device configured to collect imaging data at a distal end. The imaging probe is further configured to be slidable through one of the plurality of lumens not receiving the first probe and positionable to collect imaging data at a distal end of the insertion tube. A second electrically-conductive elongated probe is electrically connectable to a second pole of the electrical power source. The second probe is slidably receivable through one of the plurality of lumens not receiving the first probe and has a distal end insertable into the target tissue.

In another illustrative embodiment, a system includes an electrical power source having poles across which an electrical current is selectively applied. An imaging device is configured to receive an output of an imaging sensor and display imaging data collected by the imaging sensor. An insertion tube defines therein lumens. The insertion tube is configured to slide through a bodily orifice and into a bodily passageway to a target tissue. A first electrically-conductive elongated probe is electrically connectable to a first pole of an electrical power source. The first probe is slidably receivable through one of the plurality of lumens and has a distal end insertable into the target tissue. An elongated imaging probe is electrically connectable to an imaging device configured to collect imaging data at a distal end. The imaging probe is further configured to be slidable through one of the plurality of lumens not receiving the first probe and is positionable to collect imaging data at a distal end of the insertion tube. A second electrically-conductive elongated probe is electrically connectable to a second pole of the electrical power source. The second probe is slidably receivable through one of the plurality of lumens not receiving the first probe and has a distal end insertable into the target tissue.

In a further illustrative embodiment, a method includes inserting an insertion tube into a bodily orifice and through a bodily passageway to a target tissue. The insertion tube defines therein lumens configured to simultaneously receive at least two of a first electrically-conductive elongated probe, a second electrically-conductive elongated probe, and an elongated imaging probe. A distal end of the insertion tube is positioned proximate a target tissue. The imaging probe is slid through one of the plurality of lumens. Imaging data is collected with the imaging probe to verify a position of a distal end of the insertion tube proximate the target tissue. The first probe is slid through one of the plurality of lumens not receiving the imaging probe to insert a distal end of the first probe into the target tissue. Imaging data is collected with the imaging probe to verify insertion of the first imaging probe into the target tissue. The second probe is slid into one of the plurality of lumens not receiving the first probe to insert a distal end of the second probe into the target tissue. Proximal ends of the first and second probes are electrically connected to an electrical power source so that an electrical current is applied to the target tissue between the distal ends of the first probe and the second probe.

Further features, advantages, and areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way. The components in the figures are not necessarily to scale, with emphasis instead being placed upon illustrating the principles of the disclosed embodiments. In the drawings.

DETAILED DESCRIPTION

The following description is merely illustrative in nature and is not intended to limit the present disclosure, application, or uses. It will be noted that the first digit of three-digit reference numbers and the first two digits of four-digit reference numbers correspond to the first digit of one-digit figure numbers and the first two digits of two-digit figure numbers, respectively, in which the element first appears.

The following description explains, by way of illustration only and not of limitation, various embodiments of an insertion tube defining lumens therein for conveying conductive probes, imaging probes, and other elongated implements to a target tissue in a body. As will be described in detail below, when used for electrosurgical techniques, the insertion tube may be used to position first and second conductive probes in or adjacent to a target tissue where electrical treatment, such as ablative treatment, is to be applied. For a specific example, described apparatuses, systems, and methods of their use may be used for ablating and/or coagulating tissue, removing lesions, and for performing other medical procedures within a lung.

It will be appreciated that various embodiments of the insertion tube and elongated implements conveyed through the insertion tube described herein may help to simplify the process of positioning the conductive probes. As will be described below, various embodiments may be used to accomplish the positioning and/or verifying the positioning of the conductive probes, as well as potentially holding the conductive probes and/or insertion tube in place.

Figure 1:
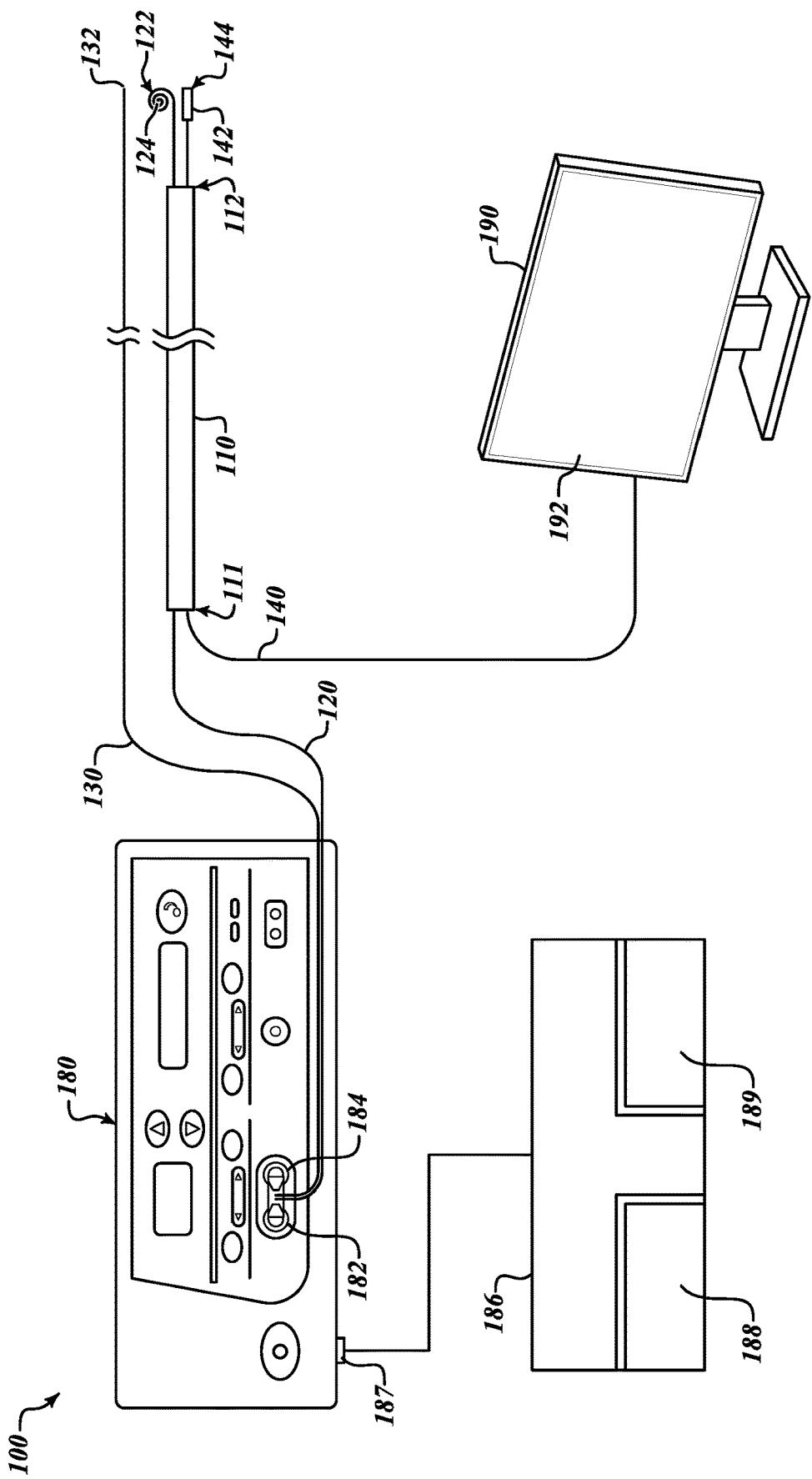
FIG. 1 is a block diagram in partial schematic form of an illustrative system for treating tissue.

Referring to FIG. 1, an illustrative system 100 is provided for treating tissue at a target region of a patient (not shown). The system 100 may be a bipolar or monopolar radio frequency (RF) system, as desired, for treating tissue in a patient. However, various embodiments described herein are configured to position two conductive probes within and/or adjacent to the target tissue to support implementation of a bipolar treatment system, thereby allowing for electric current to be selectively passed through a particular target region in a patient. Specifically, the system 100 may be employed for coagulation and/or ablation of soft tissue during percutaneous and/or endoscopic surgical procedures, such as, for example, bronchoscopic surgical procedures for partial and/or complete ablation of cancerous and/or non-cancerous organ lesions. As will be further described, the tissue is treated by positioning one or more conductive probes within and/or adjacent to the tissue to be treated and selectively passing an electrical current through the tissue.

In some embodiments, the system 100 includes an insertion tube 110 for conveying elongated implements, such as a first electrically-conductive probe 120, a second electrically-conductive probe 130, and an imaging probe 140, to the target tissue (not shown in FIG. 1). The system 100 also includes an electrosurgical radio frequency (RF) generator operating as a switchable current source 180 and an imaging device 190, such as an ultrasound or other imaging system as desired for a particular application. If desired, an infusion pump (not shown) also may be included to supply a conductive fluid, such as saline solution, via lumens in the insertion tube 110 to the target tissue. The system 100 also may include an electrosurgical device (not shown) such as an endoscope or a bronchoscope configured to receive the insertion tube 110 therein. The electrosurgical device may be used to convey the insertion tube 100 into a body (not shown) proximate to a bodily passage that may be too narrow to receive a distal end (not shown) of the electrosurgical device, but into which the insertion tube 110 may pass.

The conductive probes 120 and 130 may be joined with the switchable current source 180 via connectors 182 and 184, respectively, or the conductive probes 120 and 130 may be connected to poles of the switchable current source 180 using a single, bipolar connector (not shown). The switchable current source 180 may be operated with the use of a foot-operated unit 186 electrically connected to the switchable current source 180. The foot-operated unit 186 may include, for example, a first pedal 188 that directs the switchable current source 180 to apply an electrical current to the conductive probes 120 and 130 to cut, ablate, or otherwise treat tissue and a second pedal 189 that instructs the switchable current source 180 to apply a lower electrical current to the one or more conductive probes 120 and 130 to coagulate tissue. It will be appreciated that the switchable current source 180 may be any number of suitable current sources and the switchable current source 180 may be controlled by any number of hand-operated, foot-operated, computer-controlled devices, or any other form of activation devices.

The imaging device 190 may include a display configured to visually present, in color or in monochrome, imaging data collected by the imaging probe 140. In various embodiments, the imaging device 190 includes an ultrasound system having a display screen 192 that displays imaging data collected by an imaging head 142 at a distal end 144 of the imaging probe 140. In various embodiments, the imaging probe 140 and the imaging system 190 provide a visualization of imaging data collected in a 360-degree or other panoramic view around the imaging head 140. As explained further below, the imaging probe 140 and the imaging system 190 are usable to collect imaging data to verify a position of the insertion tube 110 and/or one or more of the conductive probes 120 and 130 relative to a target tissue.

As further described below with reference to FIGS. 3-15, in various embodiments the insertion tube 110 defines therein lumens through which the conductive probes 120 and 130 and the imaging probe 140 are slidably extended into a proximal end 111 of the insertion tube 110. The conductive probes 130 are extended through a length of the insertion tube 110 to reach a distal end 112 of the insertion tube 110 that is to be positioned adjacent the target tissue (not shown in FIG. 1). As also described below, in various embodiments, the distal end 112 of the insertion tube 110 is slidable through a bodily passageway, such as a bronchial passageway, a gastrointestinal passageway, or another passageway, and positionable adjacent the target tissue.

The position of the distal end 112 of the insertion tube 110 relative to the target tissue may be optionally verified by extending the imaging head 144 of the imaging probe 140, slidably received in one of the lumens of the insertion tube 110, beyond the distal end 112 of the insertion tube 110. The imaging device 190 may then be used to review imaging data collected by the imaging probe 140 to assess whether the insertion tube 110 has been deployed as desired relative to the target tissue.

A first conductive probe 120 may then be extended beyond the distal end 112 of the insertion tube 110 to position a distal end 122 of the first conductive probe 120 into or near the target tissue. The distal end 122 of the first conductive probe 120 may include a coiled section 124, as further described below. The position of the distal end 122 of the first conductive probe 120 may be verified using the imaging probe 140.

A distal end 132 of the second conductive probe 130 may then be extended beyond the distal end 112 of the insertion tube 100 into or near the target tissue. To extend the second conductive probe 130, the imaging probe 140 may be withdrawn from the lumen in the insertion probe 110 through which it was extended and the second conductive probe 130 may be extended through that same lumen. Alternatively, if the insertion tube 110 defines more than two lumens therethrough, the second conductive probe 130 may be extended through an additional lumen to reach the target tissue. The imaging probe 140 then may be used to verify the position of the second conductive probe 130. If the imaging probe 140 remains deployed through another lumen, it will be appreciated that the imaging probe 140 desirably may be partially withdrawn into the insertion tube 110 before electrical current is applied through the conductive probes 120 and 130. Withdrawal of the imaging probe 140 may prevent damage to the imaging probe 140 or to prevent electrical current intended for the target tissue to be redirected through the imaging probe 140. This process is depicted and described in more detail below with reference to FIGS. 7 through 15.

Figure 2:
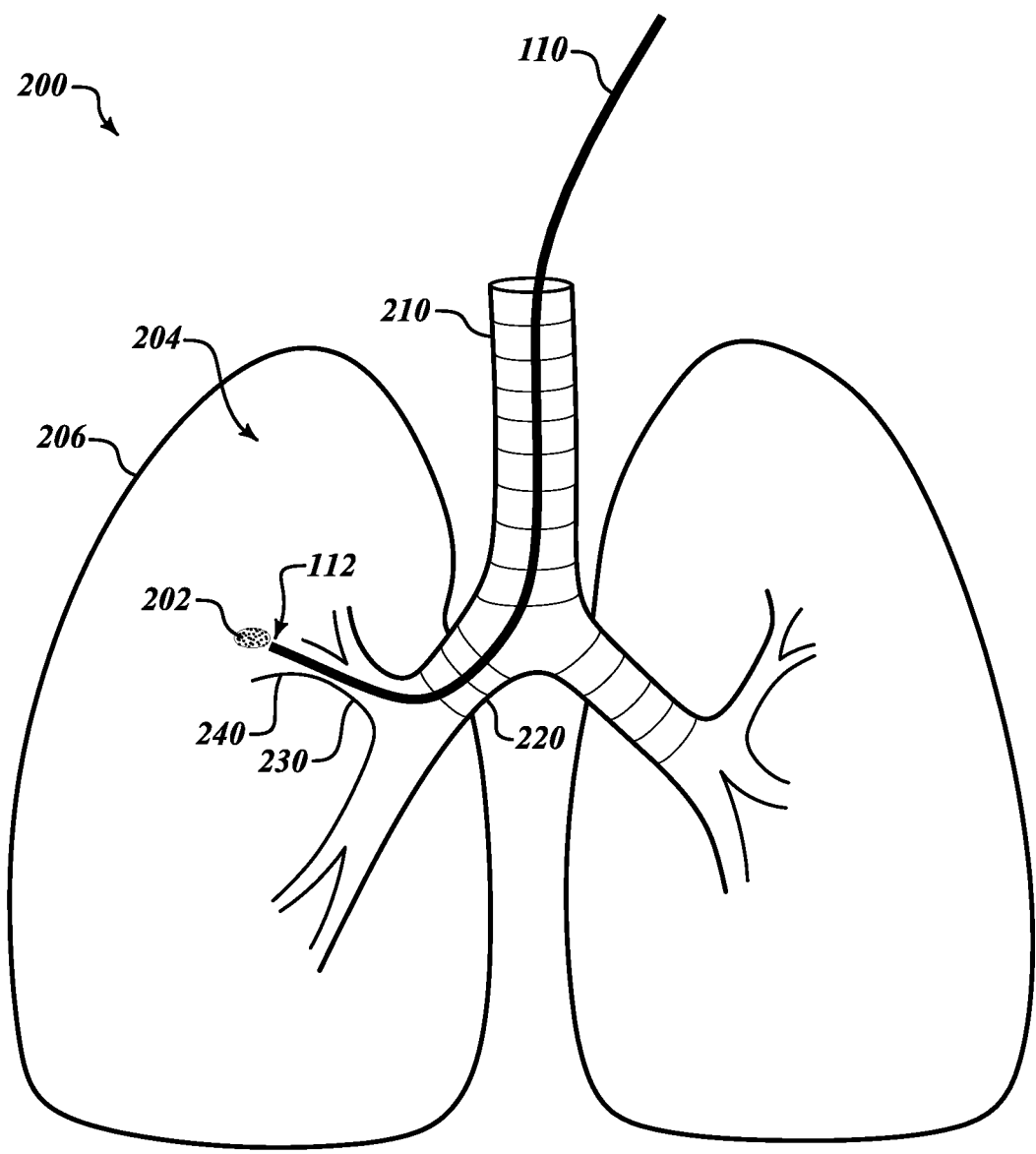
FIG. 2 is a schematic diagram in partial cutaway form of an apparatus inserted into a peripheral bronchial passageway of a lung.

Referring to FIG. 2, apparatuses, systems, and methods of the present disclosure may be utilized with regard to treatment of a target tissue 202 within a human respiratory system 200. In particular, the target tissue 202 is in an upper lobe 204 of a right lung 206 (the view of the respiratory system 200 is with the subject facing out of the page of FIG. 2) of the respiratory system 200. The insertion tube 110 is inserted into the respiratory system 200 through a patient's mouth (not shown in FIG. 2). The insertion tube 110 is extended through a trachea 210 into the right lung 206 via a primary bronchial passageway 220. The insertion tube 110 further extends through a secondary bronchial passageway 230 and a peripheral bronchial passageway 240, where the distal end 112 of the insertion tube 110 is positioned adjacent to the target tissue 202. With the distal end 112 of the insertion tube 110 positioned adjacent to the target tissue 202, the probes 120, 130, and 140 (not shown in FIG. 2) may be extended adjacent to and/or into the target tissue 202. As previously mentioned with reference to FIG. 1, the insertion tube 110 may be conveyed and maneuvered through the trachea 210, the primary bronchial passageway 220, and or the secondary bronchial passageway 230 using an electrosurgical device, such as a bronchoscope (not shown). The insertion tube 110 may then be slidably extended beyond an end of the electrosurgical device into the secondary bronchial passageway 220 and/or the peripheral bronchial passageway 230.

Referring to FIGS. 3-6, elongated implements, such as the probes 120, 130, and 140, are slidably received in and extended through lumens 310 and 320 in the insertion tube 110. FIGS. 3-6, as well as FIGS. 7-15, depict a distal portion 300 of the insertion tube 110. In various embodiments, the insertion tube 110 and the lumens 310 and 320 are uniform through the length of the insertion tube 110, thus, the distal portion 300 is representative of the structure and function of the insertion tube 110 as a whole.

Figure 3:
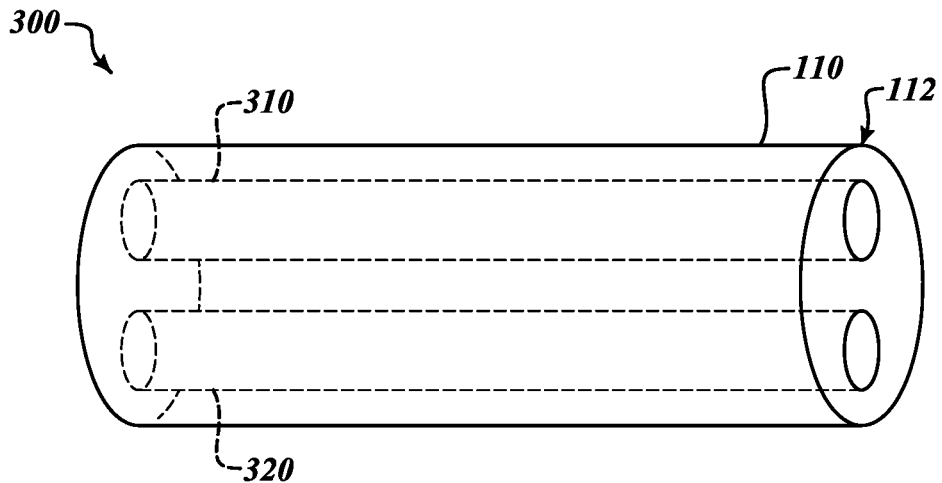
FIG. 3 is a perspective view in partial cutaway form of a distal portion of an insertion tube.

Referring to FIG. 3, the distal portion 300 of the insertion tube 110 includes a first lumen 310 and a second lumen 320 defined by the insertion tube 110. The lumens 310 and 320 may be identical in size as depicted in FIG. 3, or they may have unequal sizes to accommodate different probes or other implements. Also, while both lumens 310 and 320 are depicted in FIGS. 3-15 as being cylindrical in shape, various embodiments may include lumens with rectangular cross-sections, triangular cross-sections, or other shapes as may be appropriate to receive and/or maintain an orientation of probes or other implements received therein. The lumens 310 and 320 extend from a proximal end 111 (FIG. 1) of the insertion tube 110 to the distal end 112 of the insertion tube 110. In various embodiments, the insertion tube 110 defines two lumens, including the first lumen 310 and the second lumen 320, but, in other embodiments, the insertion tube may define three or more lumens.

Figure 4:
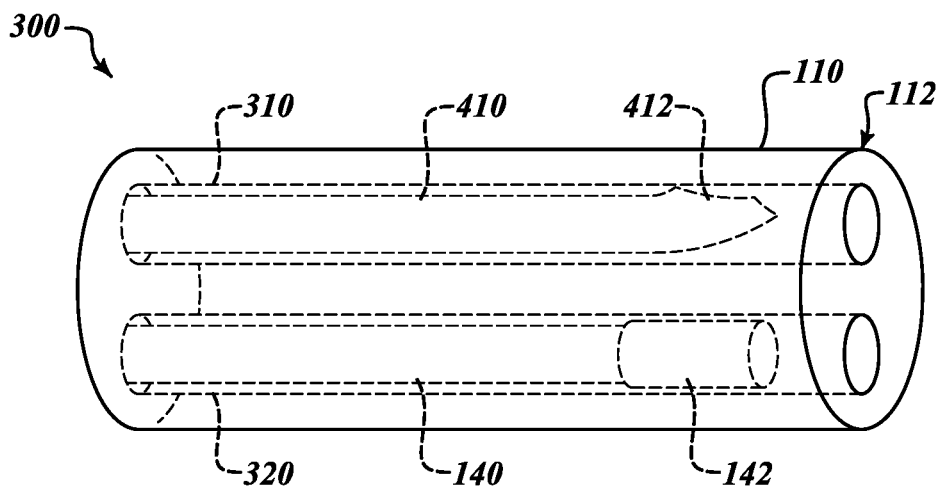
FIGS. 4-6 are perspective views in partial cutaway form of the distal portion of the insertion tube of FIG. 3.

Referring to FIG. 4, the lumens 310 and 320 of the distal portion 300 of the insertion tube 110 receive therein a pair of illustrative implements 410 and 140. The second lumen 320 receives the imaging probe 140, with the imaging probe 140 supporting the imaging head 142 at the distal end 144. In the example of FIG. 4, the first lumen 310 receives a sampling needle 410. The sampling needle 412 has a tip 412 that is shaped to cut or pierce tissue (not shown) and retrieve a portion of the tissue for testing. The sample may be retrieved by applying suction to a proximal end (not shown) of the sampling needle 412, or fully retracting the sampling needle 412 from the insertion tube 110 and taking the sample from the tip 412. Various embodiments of the disclosure provide for the distal end 112 of the insertion tube 110 to be positioned at or adjacent to the tissue, for the imaging head 142 of the insertion tube 140 and the tip 412 of the sampling needle 410 to be extended beyond the distal end 112 of the insertion tube 110. Using the imaging head 142 (and the imaging system 190 of FIG. 1) to monitor and guide the sampling needle 410, the insertion tube 110 is usable to collect a sample of tissue, potentially immediately before applying electrical treatment as further described below.

Figure 5:
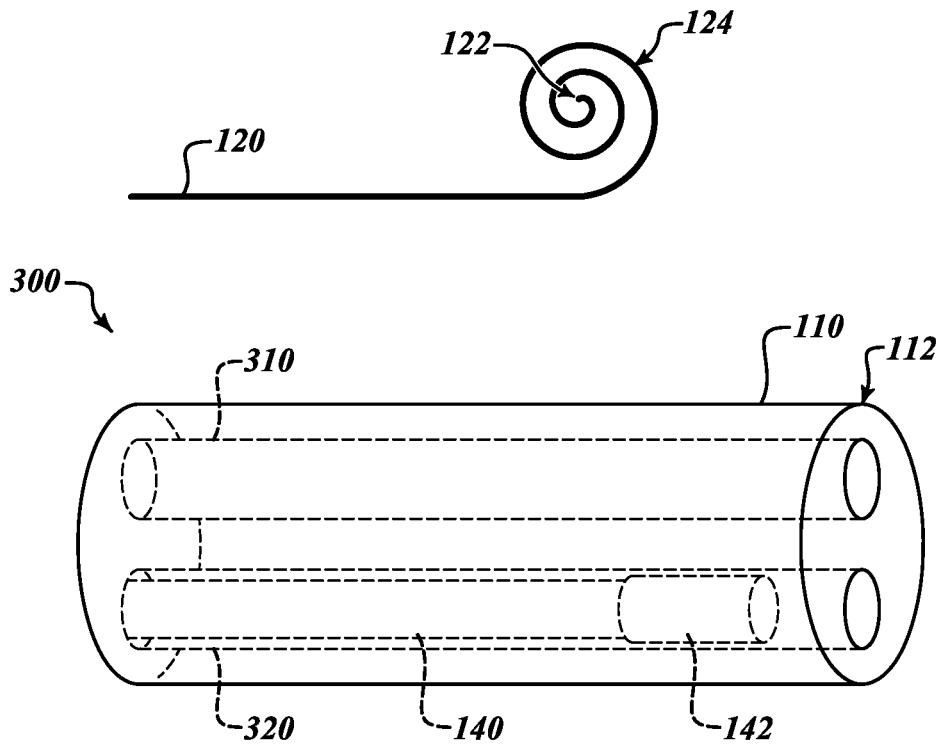

Referring to FIG. 5, while the imaging probe 140 (and the supported imaging head 142) remains in place within the second lumen 320, the first lumen 310 is empty, pending insertion of another elongated implement, such as the first conductive probe 120. As previously described with reference to FIG. 1, the first conductive probe 120 includes a coiled section 124 toward the distal end 122. In various embodiments, the first conductive probe 120, at least toward the distal end 122, is comprised of a memory wire such as nylenol. The memory wire permits the coiled section 124 to re-assume its coiled shape even after the coiled section 124 may have been constrained into a straightened form, as described below.

Figure 6:
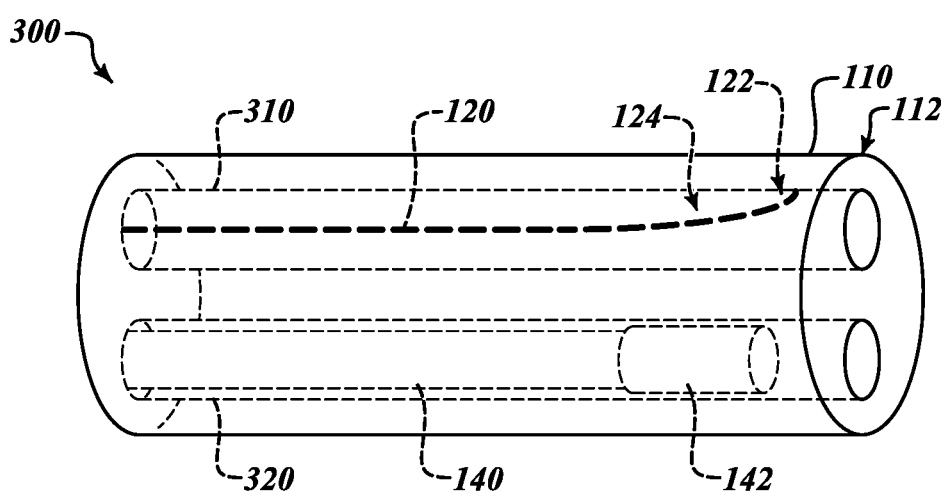

Referring to FIG. 6, with the imaging probe 140 still received within the second lumen 320, the first conductive probe 120 is received within the first lumen 310. As previously explained with reference to FIG. 5, the coiled section 124 of the first conductive probe 120, confined within the first lumen 310, is constrained to assume a straightened position. The straightening of the coiled section 124 allows the first conductive probe to be extended and retracted through the first lumen 310, while still enabling the coiled section 124 to resume its coiled shape once extended beyond the first lumen 310 at the distal end 112 of the insertion tube 110.

Referring to FIGS. 7-15, the insertion tube 110 and the probes 120, 130, and 140 are extended to and/or into the target tissue 202 to arrange for the application of electrical current in or at the target tissue 202. The positions and configurations depicted in FIGS. 7-15 represent only two examples of possible configurations and manipulations of the insertion tube 110 and the probes 120, 130, and 140. It will be appreciated that other actions could be performed, such as using the sampling needle 410 (FIG. 4) or taking other actions using the insertion tube 110 and combinations of one or more of the probes 120, 130, and 140.

Figure 7:
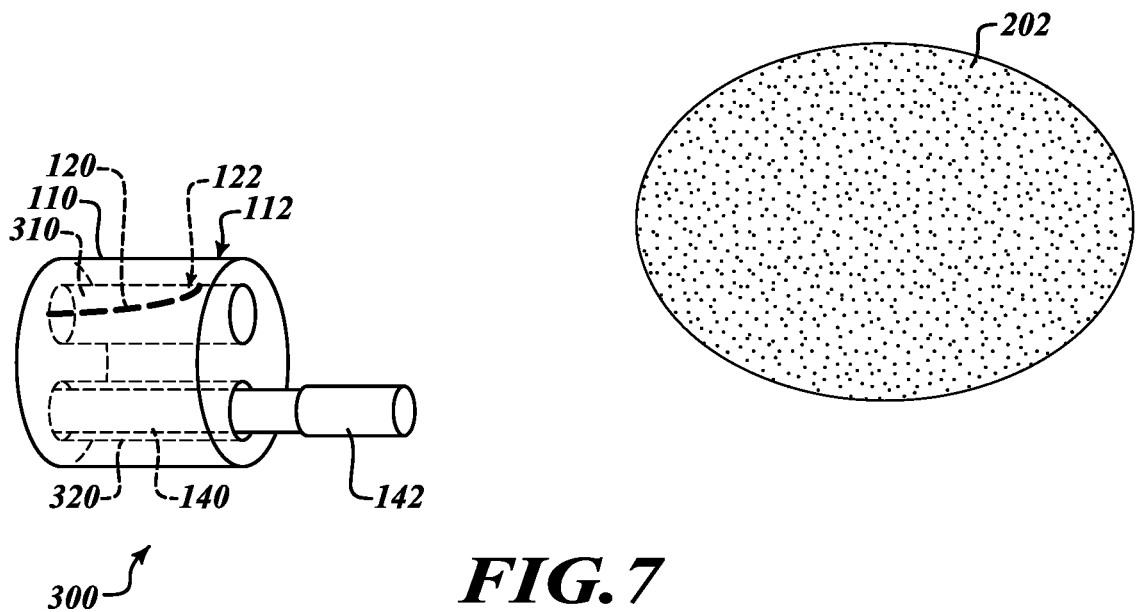
FIGS. 7-15 are perspective diagrams in partial cutaway form of the distal portion of the insertion tube of FIG. 3-6.

Referring to FIG. 7, the distal end 112 of the insertion tube 110 is prepared for extension toward the target tissue 202. In various embodiments, the first lumen 310 receives the imaging probe 140 and the second lumen 320 receives the first conductive probe 120. In various embodiments, the imaging probe 140 is partially extended from the second lumen 320 so that the imaging head 142 extends beyond the distal end 112 of the insertion tube 110. With the imaging head 142 extended, the imaging probe 140 may be used to determine the position of the distal end 112 of the insertion tube 110 relative to the target tissue 202. However, if other techniques are used to determine the position of the distal end 112 of the insertion tube 110 relative to the target tissue 202, such as ultrasound imaging performed from outside of the body (not shown), the imaging probe 140 may be partially retracted to hold the imaging head 142 within the insertion tube 110 as it is extended to the target tissue 202.

Figure 8:
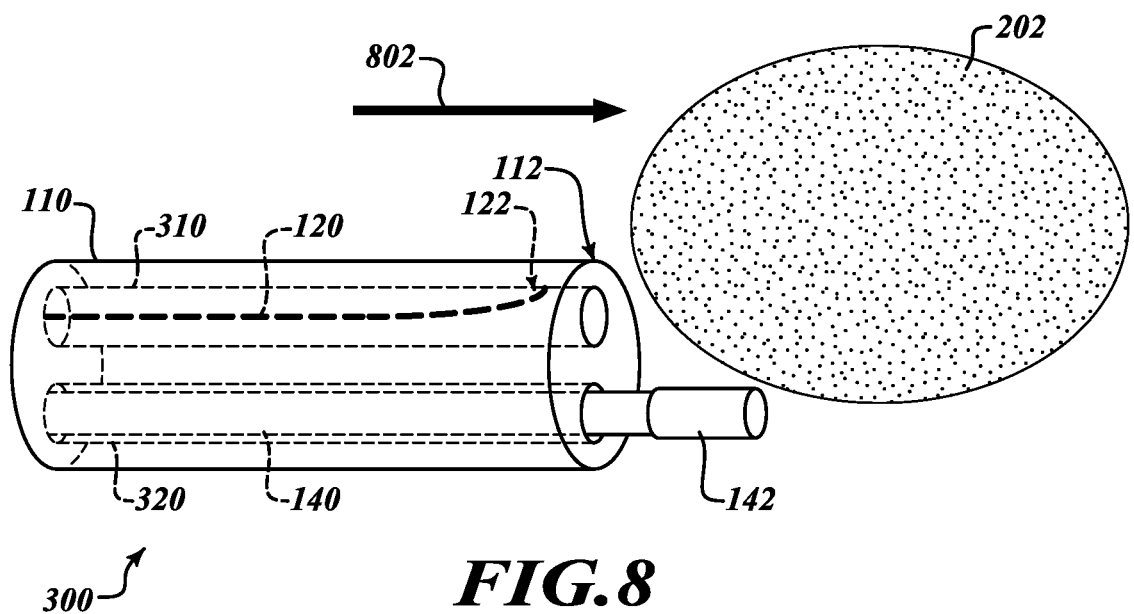

Referring to FIG. 8, the insertion tube 110 is advanced through a distance 802 so that the distal end 112 of the insertion tube 110 is positioned adjacent to the target tissue 202. The first conductive probe 120 and the imaging probe 140 received within the lumens 310 and 320 of the insertion tube 110 move in concert, at a same time and through a same distance, with the insertion tube 110 unless or until the probes 120 and 140 are individually manipulated separately from the insertion tube 110. If the imaging probe 140 has been extended so that the imaging head 142 is extended beyond the insertion tube 110 prior to the insertion tube 110 being moved, as previously described, the imaging probe 120 may be used to guide the distal end 112 of the insertion tube 110 to the desired location adjacent to the target tissue 202. Alternatively, if the insertion tube 110 is guided into place with other imaging systems, once the distal end 112 of the insertion tube 110 is in place adjacent to the target tissue 202, the imaging probe 140 may now be advanced to extend the imaging head 142 out of the insertion tube 110 for further verification of the distal end 112 of the insertion tube 110 and/or for monitoring or verifying deployment of the first conductive probe 310.

Figure 9:
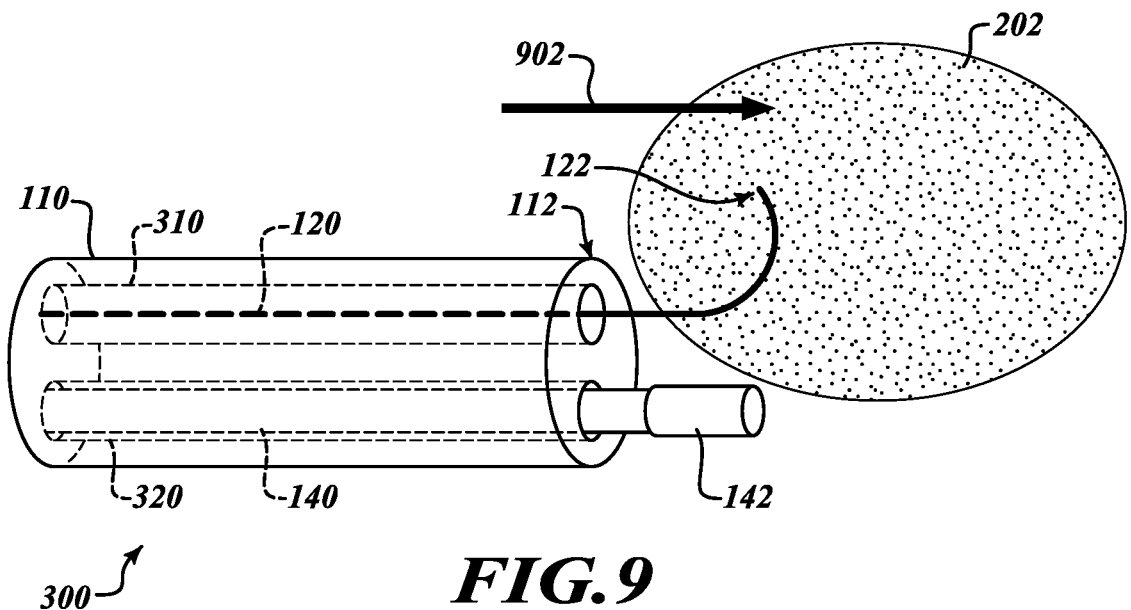

Referring to FIG. 9, the insertion tube 110 is in place with its distal end 112 adjacent to the target tissue 202 and the imaging probe 140 is extended to deploy the imaging head 142. At this point, the first conductive probe 120 is extended into the target tissue 202. The first conductive probe 120 is advanced through a linear distance 902. As previously described, adjacent to the distal end 122 of the first conductive probe 120 is the coiled section 124 (illustrated in FIG. 10). When the first conductive probe 120 is advanced into the target tissue, the coiled section 124 is no longer constrained by the first lumen 310 and can resume its coiled shape as it is extended out of the first lumen 310. The imaging head 142 of the imaging probe 140 can be used to verify that the first conductive probe 120 is in the desired position.

Figure 10:
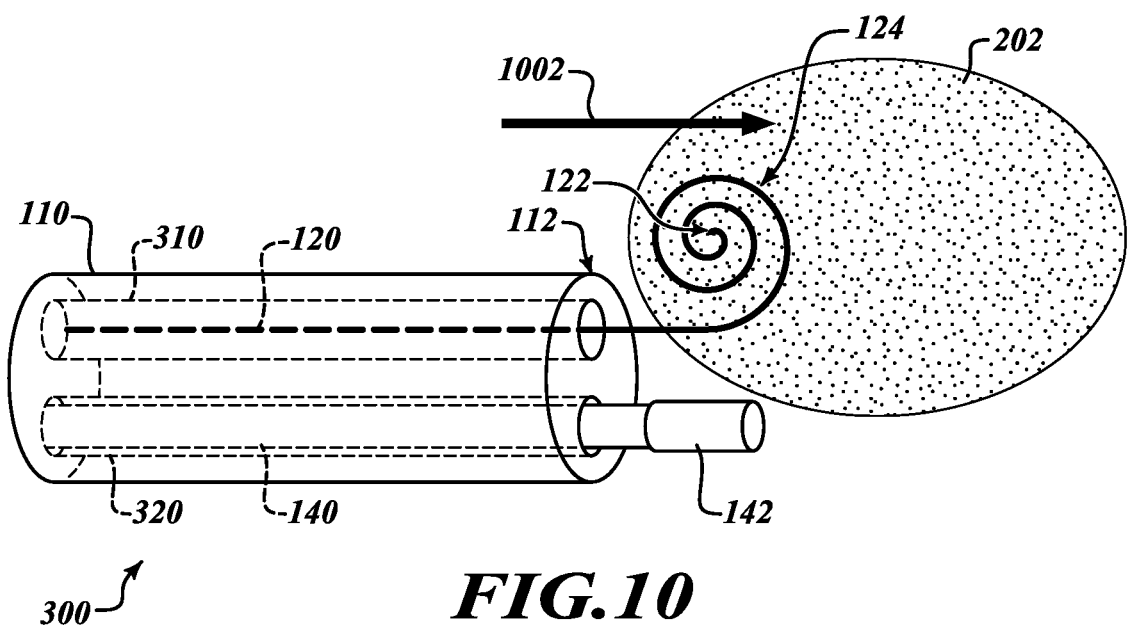

Referring to FIG. 10, the first conductive probe 120 is further extended through the first lumen 310 through a linear distance 1002, allowing the coiled section 124 of the first conductive probe 120 to fully resume its coiled shape. Again, the imaging head 142 of the imaging probe 140 can be used to verify that the first conductive probe 120 is in the desired position.

It will be appreciated that, as the first conductive probe 120 is extended, allowing the coiled section 124 to resume its coiled shape, the coiled section 124 corkscrews or augers into the target tissue 202, securing the distal end 122 of the primary conductive probe 120 into the target tissue 202. Further, because the first conductive probe 120 extends through the first lumen 310 of the insertion tube 110, the coiled section 124 maintains the distal end 112 of the insertion tube 110 in position relative to the target tissue 202.

Figure 11:
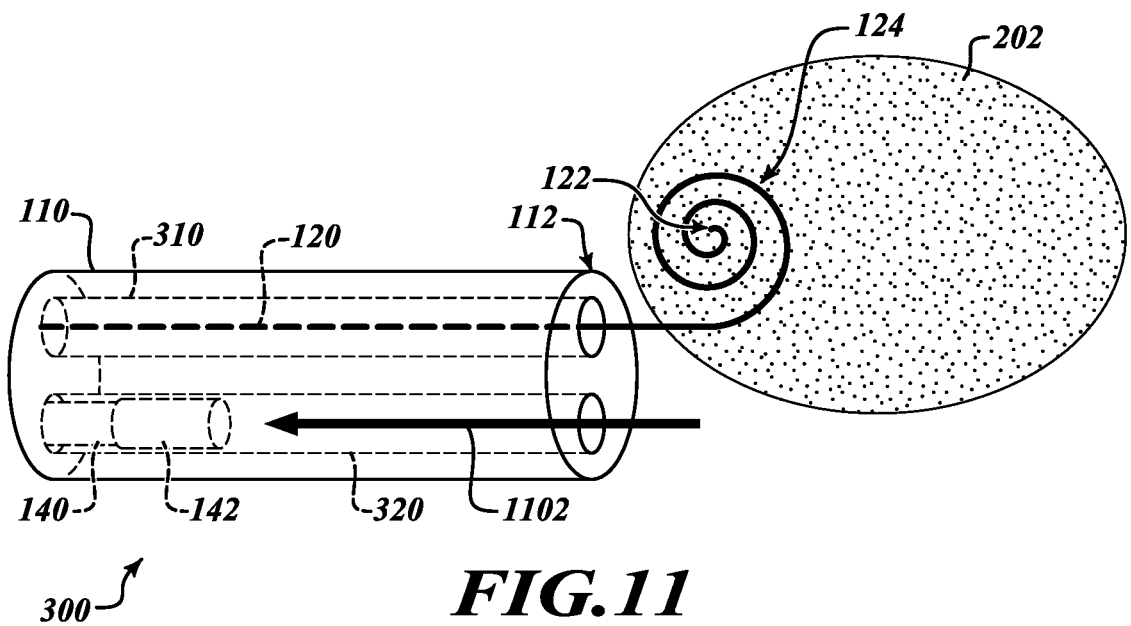

Referring to FIG. 11, with the first conductive probe 120 in place in the target tissue 202, with the coiled distal section 124 holding the first conductive probe 120 and the insertion tube 110 in place, the imaging probe 140 may be withdrawn from the second lumen 320. The imaging probe 140 is moved in a direction 1102 in FIG. 11. Continuing to move the imaging probe 140 in the direction 1102, the imaging probe 140 may be fully withdrawn from the second lumen 320, freeing the second lumen 320 to receive the second conductive probe 130.

Figure 12:
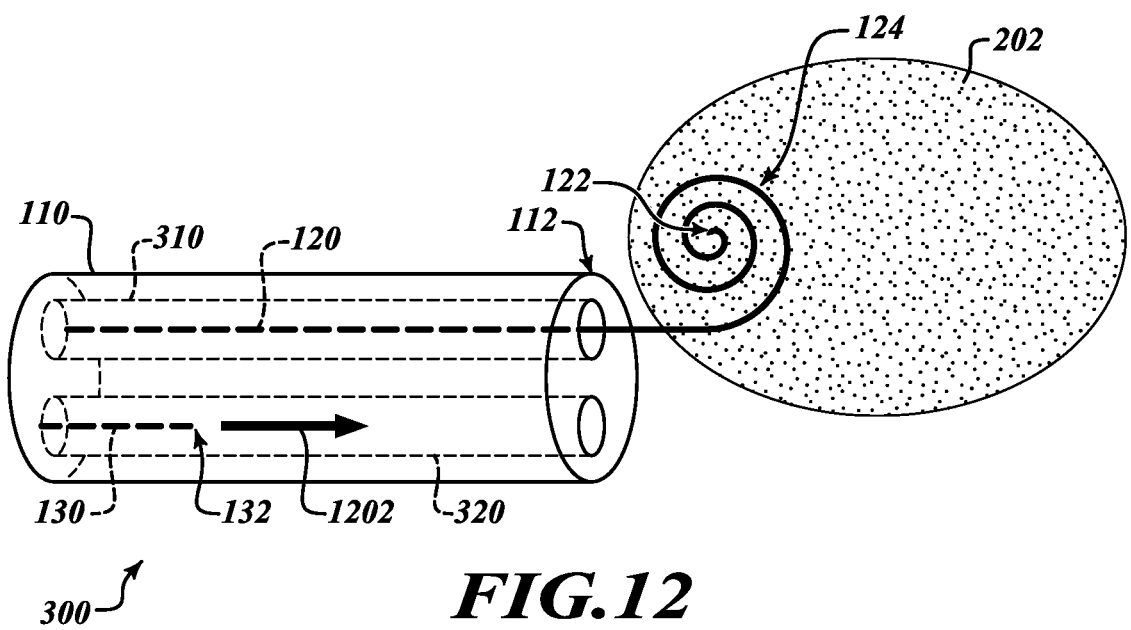

Referring to FIG. 12, the second conductive probe 130 is extended in a direction 1202 into the distal portion 300 of the insertion tube 110. With the coiled section 124 of the first conductive probe 120 in place, the distal end 112 of the insertion tube 110 is oriented so that the second lumen 320 is facing toward the target tissue 202.

Figure 13:
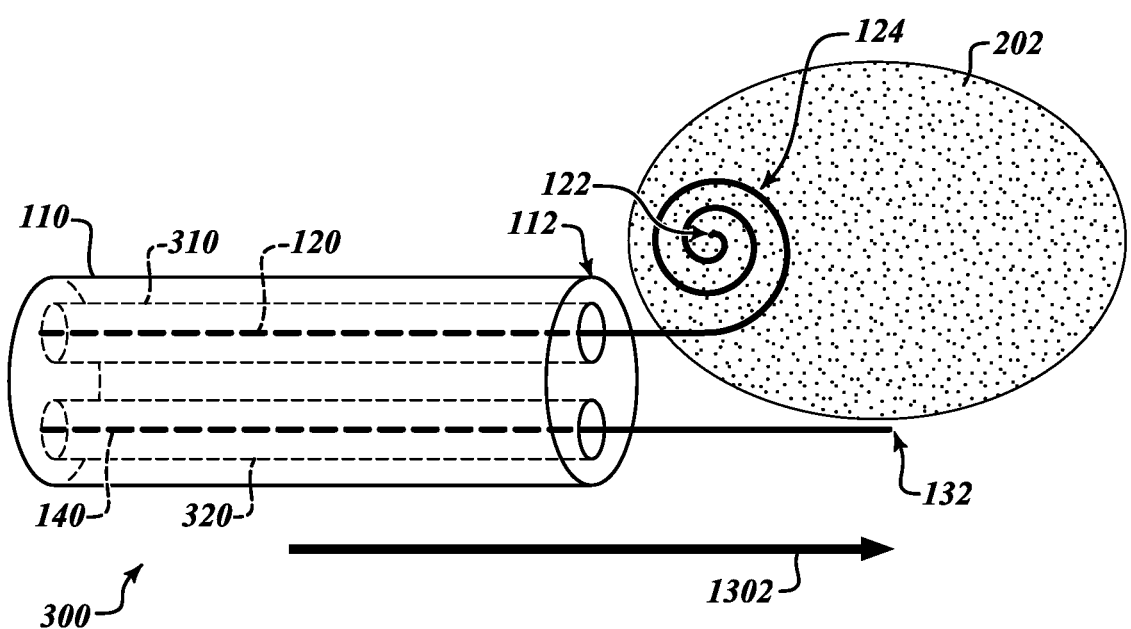

Referring to FIG. 13, the second conductive probe 130 is further extended through a distance 1302 so that the distal end 132 of the second conductive probe 130 is positioned in or adjacent to the target tissue 202. With the distal end 122 of the first conductive probe 120 inserted into the target tissue 202 and the distal end 132 of the second conductive probe 130 inserted into or positioned next to the target tissue 202, the switchable current source 180 may be activated to apply electrical power between the distal ends 122 and 132 of the conductive probes 120 and 130. The application of the electrical power thus may be used to ablate the target tissue 202, cut the target tissue 202, coagulate the target tissue 202, or perform some other treatment on the target tissue 202 in accordance with a desired application.

Although the second conductive probe 130 is depicted as a straight implement in FIGS. 1, 12, and 13, the second conductive probe also could be shaped to facilitate positioning of the second conductive probe into or adjacent to the target tissue 202. For example, the second conductive probe may include an angled portion, formed of a memory wire or simply mechanically biased into an angled position. As in the case of the coiled distal section 124 of the first conductive probe 120. The angled portion of the second conductive probe may be constrained into a generally straightened position within the second lumen 320 of the insertion tube 110, but free to deflect to reach the target tissue 202 once extended out of the second lumen 320.

Figure 14:
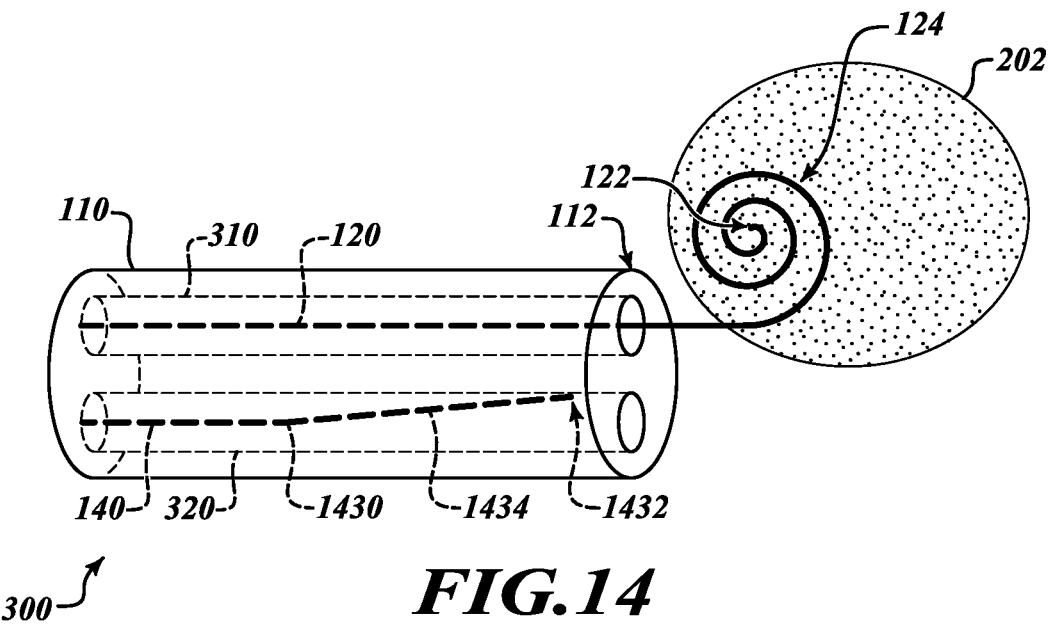

Referring to FIG. 14, the first conductive probe 120 is positioned as previously described with reference to FIGS. 9-13, with the coiled distal section 124 of the first conductive probe 120 inserted into the target tissue 202. A second conductive probe 1430, having an angled section 1434 adjacent a distal end 1432, is received within the second lumen 320 of the insertion tube 110. As previously described, the angled section 1434 is constrained into a generally straightened shape when received within the second lumen 320 of the insertion tube 110.

Figure 15:
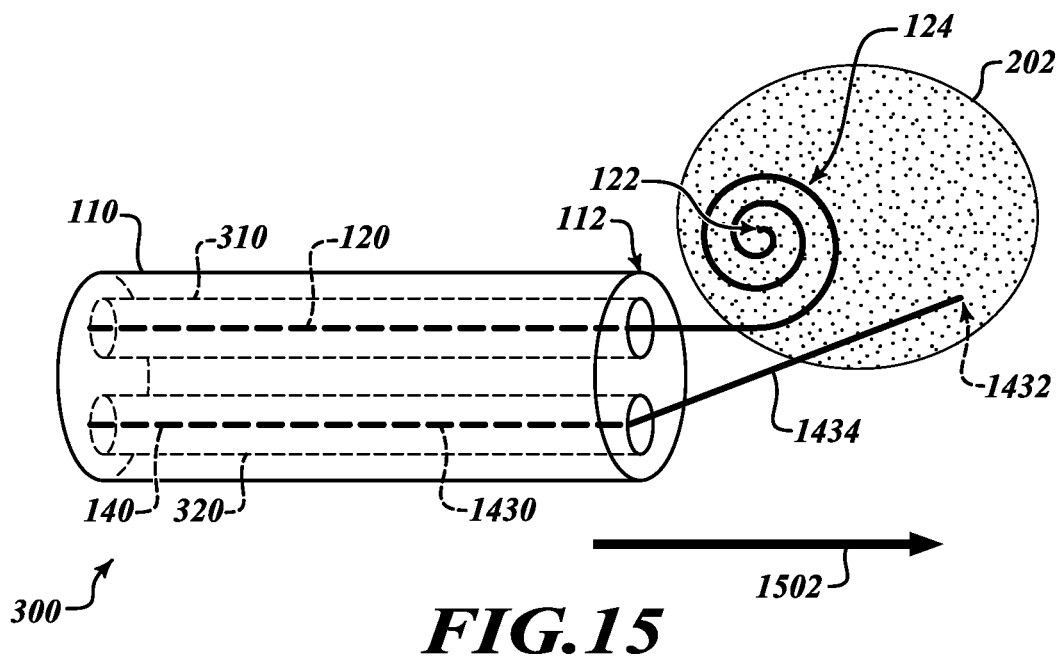

Referring to FIG. 15, the second conductive probe 1430 is advanced a distance 1502, causing the distal end 1432 of the second conductive probe 1430 to extend out of the second lumen 320, the angled section 1434 of the second conductive probe 1430 is able to resume its angled configuration. The angled section 1434 may be shaped to extend toward or into the target tissue 202.

Although not depicted in the figures or otherwise described, it will be appreciated that the insertion tube 110 and the probes, such as probes 120, 130, 140, and 1430, may be withdrawn from the body by reversing processes used to deploy the insertion tube 110 and the probes 120, 130, 140, and 1430. For example, after the insertion tube 110 and conductive probes 120 and 130 are used to apply electrical treatment to the target tissue 202 as described with reference to FIG. 13, proximal ends (not shown in FIG. 13) of the conductive probes 120 and 130 may be mechanically moved to withdraw the distal ends 122 and 132 of the conductive probes 120 and 130 within the lumens 310 and 320, respectively, of the insertion tube 110. The insertion tube 110, as well as any electrosurgical device (not shown) which may have been used to convey the insertion tube 110 partway toward the target tissue 202, may be removed from the body (not shown).

Figure 16:
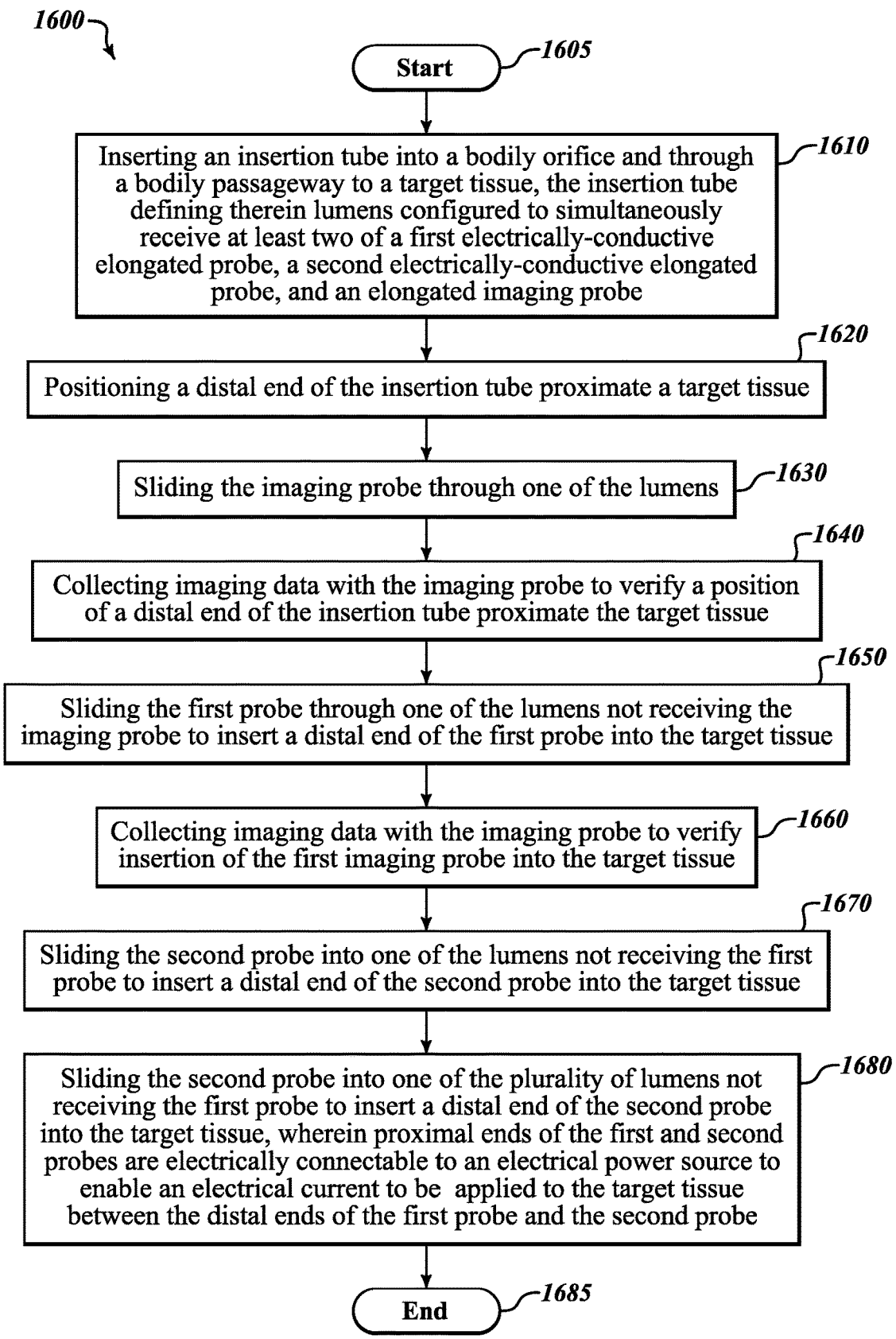
FIG. 16 is a flow diagram of an illustrative method of positioning the insertion tube and elongated implements received therethrough.

Referring to FIG. 16, a flow diagram represents an illustrative method 1600 of positioning an insertion tube and extending elongated probes therethrough for applying electrical power to treat a target tissue. The method 1600 starts at a block 1605. At a block 1610, an insertion tube is inserted into a bodily orifice and through a bodily passageway to a target tissue. The insertion tube defines therein lumens configured to simultaneously receive at least two of a first electrically-conductive elongated probe, a second electrically-conductive elongated probe, and an elongated imaging probe, as described with reference to FIGS. 1, and 3-15. At a block 1620, a distal end of the insertion tube id positioned proximate a target tissue, as described with reference to FIGS. 7 and 8. At a block 1630, the imaging probe is slid through one of the plurality of lumens, as previously described with reference to FIGS. 5-10. At a block 1640, imaging data is collected with the imaging probe to verify a position of a distal end of the insertion tube proximate the target tissue, as previously described with reference to FIGS. 7 and 8. At a block 1650, the first probe is slid through one of the plurality of lumens not receiving the imaging probe to insert a distal end of the first probe into the target tissue, as previously described with reference to FIGS. 7-15. At a block 1660, imaging data is collected with the imaging probe to verify insertion of the first imaging probe into the target tissue, as previously described with reference to FIGS. 9 and 10. At a block 1670, the second probe is slid into one of the plurality of lumens not receiving the first probe to insert a distal end of the second probe into the target tissue, as previously described with reference to FIGS. 12-13 and 15. At a block 1680, proximal ends of the first and second probes are electrically connected to an electrical power source such that an electrical current is applied to the target tissue between the distal ends of the first probe and the second probe, as previously described with reference to FIGS. 1 and 13. The method 1600 ends at a block 1685.

It will be appreciated that the detailed description set forth above is merely illustrative in nature and variations that do not depart from the gist and/or spirit of the claimed subject matter are intended to be within the scope of the claims. Such variations are not to be regarded as a departure from the spirit and scope of the claimed subject matter.

What is claimed is:

1. An apparatus comprising:
an insertion tube defining therein a pair of lumens, the insertion tube being configured to slide through a bodily orifice and into a bodily passageway to a target tissue;
a first probe electrically connectable to a first pole of an electrical power source, the first probe being slidably receivable through a first lumen of the pair of lumens and having a distal end insertable into the target tissue, wherein the first probe is configured to extend into the target tissue and anchor a distal end of the insertion tube adjacent the target tissue upon deployment;
an imaging probe electrically connectable to an imaging device configured to collect imaging data at a distal end, the imaging probe being further configured to be slidable through a second lumen of the pair of lumens not receiving the first probe and positionable to collect imaging data at a distal end of the insertion tube, wherein the imaging probe is configured to image the first probe to guide-insertion into the target tissue;
a second electrically-conductive elongated probe electrically connectable to a second pole of the electrical power source, the second probe being slidably receivable through the second lumen in exchange for the imaging probe subsequent to removal of the imaging probe from the second lumen, the second probe having a distal end insertable into tissue adjacent the first probe anchored in the target tissue to apply a treatment in conjunction with the first probe;
wherein the first and second probes are configured to perform ablation.

2. The apparatus of claim 1, wherein the imaging probe is configured to be received within the second lumen to collect imaging data used in positioning in the distal end of the insertion tube adjacent the target tissue and in confirming insertion of the distal end of the first probe through the first lumen into the target tissue.

3. The apparatus of claim 2, wherein the second probe is configured to be inserted into the second lumen after removal of the imaging probe from the second lumen to permit insertion of the second probe through the second lumen into the target tissue.

4. The apparatus of claim 1, wherein one of the pair of lumens is further configured to slidably receive an elongated sampling needle configured to collect a sample of the target tissue.

5. The apparatus of claim 1, wherein the distal end of the first probe includes a coiled section that is configured to be confinable in a straightened shape within the lumen into which the first probe is received and further configured to be coilable into a coiled shape while out of the distal end of the lumen.

6. The apparatus of claim 5, wherein the coiled section of the first probe is configured to auger into the target tissue while out of a distal end of the lumen.

7. The apparatus of claim 6, wherein the coiled section of the first probe augered into the target tissue anchors the distal end of the insertion tube adjacent the target tissue.

8. The apparatus of claim 1, wherein the distal end of the second probe includes an angled section that that is configured to be confinable in a straightened shape within the lumen into which the second probe is received and further configured to be deformable into an angled shape while out of a distal end of the lumen.

9. A system comprising:
an electrical power source having poles across which an electrical current is selectively applied; an imaging device configured to receive an output of an imaging sensor and display imaging data collected by the imaging sensor;
an insertion tube defining therein a pair of lumens, the insertion tube being configured to slide through a bodily orifice and into a bodily passageway to a target tissue;
a first probe electrically connectable to a first pole of an electrical power source, the first probe being slidably receivable through a first lumen of the pair of lumens and having a distal end insertable into the target tissue, wherein the first probe and the first lumen are configured to enable extension of the first probe into the target tissue and anchoring of a distal end of the insertion tube adjacent the target tissue upon deployment of the first probe;
an imaging probe electrically connectable to the imaging device configured to collect imaging data at a distal end, the imaging probe being further configured to be slidable through a second lumen of the pair of lumens and positionable to collect imaging data at a distal end of the insertion tube to guide insertion of the first probe into the target tissue;
a second probe electrically connectable to a second pole of the electrical power source, the second probe being slidably receivable through the second lumen in exchange for the elongated imaging probe subsequent to removal of the imaging probe from the second lumen, the second probe having a distal end insertable into tissue adjacent the first probe anchored in the target tissue to apply a treatment in conjunction with the first probe;
wherein the first and second probes are configured to perform ablation.

10. The system of claim 9, wherein the imaging probe is configured to be received within the second lumen to collect imaging data used in positioning in the distal end of the insertion tube adjacent the target tissue and in confirming insertion of the distal end of the first probe through the first lumen into the target tissue.

11. The system of claim 10, wherein the second probe is configured to be inserted into the second lumen after removal of the imaging probe from the second lumen to permit insertion of the second probe through the second lumen into the target tissue.

12. The system of claim 9, wherein the distal end of the first probe includes a coiled section that is configured to be confinable in a straightened shape within the lumen into which the first probe is received and further configured to be coilable into a coiled shape while out of the distal end of the lumen.

13. A method comprising:
inserting an insertion tube into a bodily orifice and through a bodily passageway to a target tissue, the insertion tube defining therein a pair of lumens configured to simultaneously receive at least two of a first electrically-conductive elongated probe (first probe),
a second electrically-conductive elongated probe (second probe), and an elongated imaging probe (imaging probe);
positioning a distal end of the insertion tube proximate a target tissue; sliding the imaging probe through one of the pair of lumens;
collecting imaging data with the imaging probe to verify a position of a distal end of the insertion tube proximate the target tissue;
sliding the first probe through one of the pair of lumens not receiving the imaging probe to insert a distal end of the first probe into the target tissue;
anchoring the first probe in the target tissue to secure a position of the distal end of the insertion tube adjacent the target tissue;
collecting imaging data with the imaging probe to verify insertion of the first probe into the target tissue;
after collecting the imaging data to verify the insertion of the distal end of the first probe into the target tissue, replacing the imaging probe in the one of the pair of lumens with the second probe by sliding the second probe into the one of the pair of lumens not receiving the first probe to insert a distal end of the second probe into tissue adjacent the first probe anchored in the target tissue; and
electrically connecting proximal ends of the first and second probes to an electrical power source so that an electrical current is applied to the target tissue between the distal ends of the first probe and the second probe;
wherein the first and second probes are configured to perform ablation.

* * * * *